(12) United States Patent
Albalat

(10) Patent No.: US 10,107,575 B2
(45) Date of Patent: Oct. 23, 2018

(54) FLUID WARMING OR COOLING SYSTEM

(75) Inventor: Alberto Martinez Albalat, Ajalvir Madrid (ES)

(73) Assignee: COMBAT MEDICAL HOLDINGS LTD, Wheathampstead (GB)

( * ) Notice: Subject to any disclaimer, the term of this patent is extended or adjusted under 35 U.S.C. 154(b) by 428 days.

(21) Appl. No.: 14/124,011

(22) PCT Filed: Jun. 8, 2012

(86) PCT No.: PCT/EP2012/060930
§ 371 (c)(1),
(2), (4) Date: Dec. 18, 2013

(87) PCT Pub. No.: WO2012/168451
PCT Pub. Date: Dec. 13, 2012

(65) Prior Publication Data
US 2014/0124187 A1    May 8, 2014

(30) Foreign Application Priority Data

Jun. 9, 2011   (GB) .................................. 1109657.5

(51) Int. Cl.
| F28F 21/06 | (2006.01) |
| A61M 5/44 | (2006.01) |
| B21D 5/00 | (2006.01) |
| F28F 21/08 | (2006.01) |

(52) U.S. Cl.
CPC ............. *F28F 21/065* (2013.01); *A61M 5/44* (2013.01); *B21D 5/00* (2013.01); *F28F 21/08* (2013.01)

(58) Field of Classification Search
CPC .......... F28F 21/065; F28F 21/08; A61M 5/44; B21D 5/00

USPC .................................... 165/46; 604/113, 114
See application file for complete search history.

(56) References Cited

U.S. PATENT DOCUMENTS

| 4,072,188 A * | 2/1978 | Wilson | F28F 3/12 165/185 |
| 4,473,739 A | 9/1984 | Scheiwe et al. | |
| 4,782,212 A * | 11/1988 | Bakke | A61M 5/44 165/170 |
| 4,847,470 A * | 7/1989 | Bakke | A61M 5/44 165/170 |

(Continued)

FOREIGN PATENT DOCUMENTS

| EP | 4002365 A | 1/1992 |
| EP | 0928027 A2 | 7/1999 |
| WO | 2011113421 A2 | 9/2011 |

OTHER PUBLICATIONS

International Search Report dated Aug. 31, 2012.

*Primary Examiner* — Raheena R Malik
(74) *Attorney, Agent, or Firm* — Cooper Legal Group LLC

(57) ABSTRACT

The present invention relates to a multilayer fluid heat exchanger container comprising a thermo-conductive sheet, said sheet comprising at least a first layer comprising a metal foil and at least a second layer comprising a biocompatible plastic material, a multilayer sheet for the fluid container and systems for heating or cooling a fluid comprising the container and a fluid heating or cooling device for receiving the container. The present invention further relates to methods for heating or cooling a fluid comprising the step of circulating a fluid through the container and a process for the manufacture of the fluid container.

18 Claims, 10 Drawing Sheets

(56) References Cited

U.S. PATENT DOCUMENTS

| | | | | |
|---|---|---|---|---|
| 5,205,348 A * | 4/1993 | Tousignant | F28F 3/12 165/170 |
| 5,245,693 A * | 9/1993 | Ford | A61M 5/44 165/169 |
| 5,381,510 A * | 1/1995 | Ford | A61M 5/44 165/169 |
| 5,634,269 A * | 6/1997 | Lowenstein | F28D 1/035 29/890.039 |
| 5,690,614 A | 11/1997 | Carr et al. | |
| 6,175,688 B1 * | 1/2001 | Cassidy | A61M 5/44 392/470 |
| 7,289,724 B2 * | 10/2007 | Furnrohr | A61M 1/0281 392/470 |
| 7,316,666 B1 | 1/2008 | Entenman et al. | |
| 7,853,131 B2 * | 12/2010 | Augustine | A61F 7/0085 392/470 |
| 8,620,149 B2 * | 12/2013 | Entenman | A61F 7/0085 165/167 |
| 2003/0077079 A1 * | 4/2003 | Augustine | A61M 5/44 392/470 |
| 2004/0026068 A1 * | 2/2004 | Schmidt | A61M 5/44 165/46 |
| 2004/0050532 A1 * | 3/2004 | Yamaguchi | F24J 2/208 165/46 |
| 2006/0021745 A1 * | 2/2006 | Fritze | B29C 65/02 165/172 |
| 2007/0068651 A1 * | 3/2007 | Gammons | A61F 7/02 165/46 |
| 2008/0063771 A1 * | 3/2008 | Dumm | A23L 3/20 426/522 |
| 2008/0262409 A1 * | 10/2008 | Derrico | A61M 5/44 604/19 |
| 2009/0031659 A1 * | 2/2009 | Kalfon | E04B 1/803 52/404.1 |
| 2009/0061164 A1 * | 3/2009 | Pasbrig | B29C 67/0029 428/178 |
| 2009/0101322 A1 * | 4/2009 | Hahmann | F28F 21/065 165/168 |
| 2010/0021148 A1 * | 1/2010 | Theilacker-beck | A61M 5/36 392/443 |
| 2014/0004284 A1 * | 1/2014 | Inaba | B32B 27/08 428/35.2 |

* cited by examiner

FIG. 2
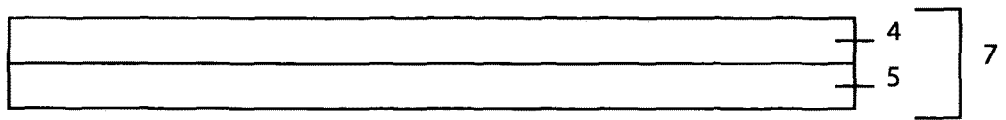
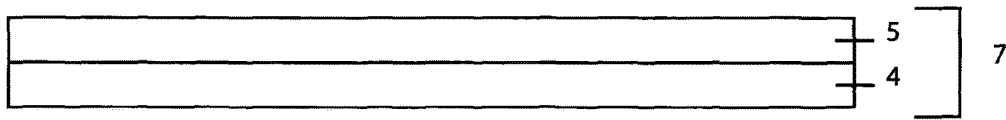
FIG. 3
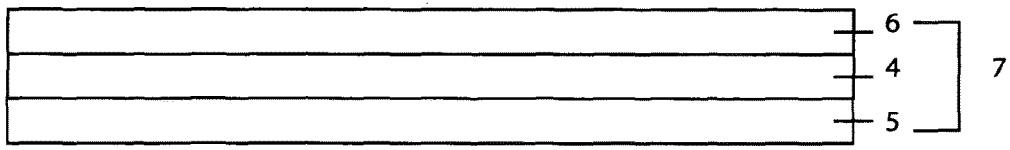
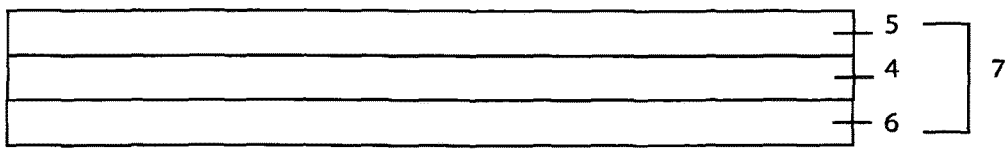

6 Polyamide 25 microns

4 Aluminium 45 microns

5 P.V.C 60 microns

FLUID WARMING OR COOLING SYSTEM

The present invention relates to a system and a method for the delivery of heated or cooled therapeutic fluids.

Systems designed to heat or cool and deliver therapeutic fluids are widely known and described in the art. These systems generally combine an electronic warming unit containing heating plates or electronic cooling device or a bath of warmed or cooled fluid, and a disposable heat exchanger container. The use of containers configured as "cassettes" to act as heat exchangers has also been described. The containers are commonly made by at least two layers of plastic material which are welded to each other using methods such as thermal or high frequency welding to define a fluid path between the two layers.

Plastic is often a preferred material because it is relatively inexpensive, it is easy to mould and manipulate. However, the majority of known plastic materials do not conduct heat efficiently. On one hand, in view of the poor conductivity of plastic materials, it is preferable for the plastic sheets forming the container to be as thin as possible. On the other hand the plastic sheets should be thick enough to warranty the homogeneity during the manufacturing process and safety (for example the absence of leaks) during the intended end use. In addition, the limitations on the thickness of the plastic layers affects the rigidity of the resulting container, which often require to be reinforced with an external rigid frame to enable positioning and insertion into the warming unit.

An alternative to plastic container is metallic containers which normally offer better performance than plastic containers in terms of thermal conductivity, but they are more expensive, more difficult to manipulate and less biocompatible. Metallic containers are more rigid and do no usually need reinforcing frames, but this rigidity creates manufacturing complications, in particular because the surface of the container contacting the heating plate of the warming device must be flat to ensure a good fit and with sufficient contact surface to provide effective heat transfer between the two elements.

It is an object of this invention to mitigate problems such as those described above.

The invention will be further described with reference to the drawings and figures, in which:

FIG. 2 is a schematic representation of a first multilayer structure for a fluid warming or cooling cassette according to the present invention;

FIG. 3 is a schematic representation of a second multilayer structure for a fluid warming or cooling cassette according to the present invention;

The heat exchanger container according to the present invention comprises a combination of plastic and metallic layers and is used in combination with an electronic warming device or an electronic cooling device or a bath of warmed or cooled fluid. The container may be used in combination with a fluid warming unit comprising heating plates or with a cooling unit comprising cooling plates. Cooling systems are for example particularly useful in neurological protection after a cardiac arrest or during cardiac surgery to cool down patient's blood for a period of time before warming it up to normal temperature under accurate control.

Figure 1:
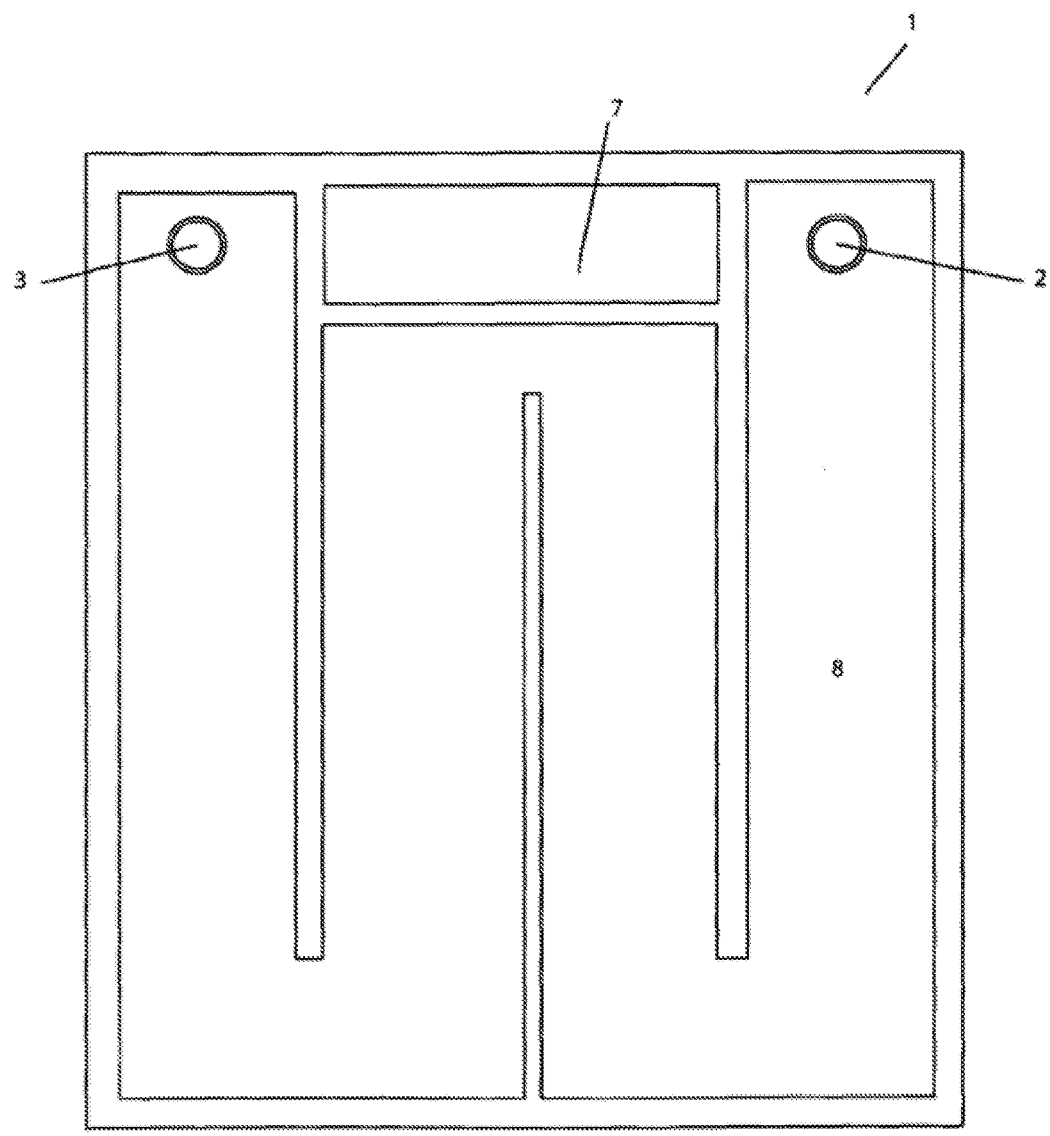
FIG. 1 is a schematic representation of a first fluid warming or cooling container according to the present invention.

Referring to FIG. 1, there is illustrated a fluid warming or cooling container 1 comprising a fluid inlet port 2 and a fluid inlet port 3. The fluid inlet port 2 is, in use, in fluid communication with a fluid reservoir, typically a therapeutic fluid bag (not shown). The fluid outlet port 3 is, in use, in connection with a patient. Biocompatible plastic tubing means, such as PVC or silicone or polyurethane tubes, may be used to connect the ports 2,3 to the fluid reservoir or to the patient.

With reference to FIGS. 2 and 3, the container comprises a first layer 4 comprising metal foil and a second internal layer 5 comprising a biocompatible plastic material.

The metal foil preferably comprises a highly conductive semi-rigid material such as an aluminium foil. More preferably, the metal foil comprises an aluminium foil (such as an aluminium soft foil) with a minimum 98% purity. Aluminium is the preferred material because it is readily available and therefore cheap. In addition, it is widely produced as a foil, which is a malleable form with good plasticity. Other highly conductive materials have been considered but copper was found to be less biocompatible, toxic and more expensive than aluminium; steel did not have as good a plasticity and conductivity; gold was more expensive.

Preferably, the thickness of the first layer 4 is less than 60 microns. A first layer 4 with a thickness of more than 60 microns would not have the required flexibility and heat transfer properties. The first layer 4 should also be thin enough to allow it to slightly expand so that good contact can be made with the heating plate. If too thick, the layer becomes too rigid and the heating plate or heat exchanger must be moved or manipulated to create enough pressure to ensure an efficient transfer of heat. The first layer 4 provides for a more effective heat transmission from the heating plates of the fluid warming unit to the therapeutic fluid (or from the therapeutic fluid to the cooling plates of the fluid cooling device) due to the presence of metallic foil. Moreover, the energy delivered to the system during the welding process of the manufacturing of the container 1 is transferred effectively and homogeneously.

Preferably, the thickness of the first layer 4 is more than 30 microns. This is because, below this range, the metal foil would not have the required rigidity to be inserted into the opening of the warming or cooling unit. The first layer 4 comprising metal foil is advantageous in that it provides the correct rigidity and consistency to the container 1. This semi-rigidity of the container 1 of the present invention, on one hand, makes the manufacture and manipulation of the container 1 easier, and, on the other hand, enables the user to insert the container 1 into a fluid warming or cooling unit. The container 1 may be used without the need of any supporting frame or structure to facilitate the insertion of the container 1 into a fluid warming or cooling unit.

It should also be noted, with respect to the preferred manufacture process, that if the first layer 4 is too thick then it becomes difficult to vacuum form the multi layer; if the first layer 4 is too thin, then the integrality of the layer becomes compromised when the structure is stretched.

More preferably, the thickness of the first layer 4 is 45 microns±8%. Ideally, the metal foil layer 4 has a thickness of approximately 45 microns and a density of approximately 121.50 $g/m^2$ for the optimum heat transfer versus rigidity balance.

The material chosen for layer 5, should be a high biocompatible material, homogeneous, easy to manipulate, inexpensive and compatible with the adhesive substances used during the laminating process (join to the metallic layer 4) and suitable for thermal or radiofrequency welding (container production process). An example of this material is PVC (preferably free of DHP).

Preferably, the thickness of the second layer 5 ranges from 45 microns to 75 microns. This is because when the internal layer 5 is thinner than 45 microns, it becomes difficult to process and to manipulate and does not provide a surface thick enough for efficient bonding or welding to the other layer(s). In addition, when the second layer is too thin, then the weld will be too weak to withstand the pressure of fluid during use and can potentially burst. When the internal layer 5 is thicker than 75 microns, the heat transfer, and consequently the performance of the system, could be reduced. The most preferred thickness for the internal layer 5 is approximately 60 microns±10%.

The internal layer 5 is the biocompatible plastic layer which, in use, comes in contact with the therapeutic fluid (e.g. fluid or blood) and therefore preferably comprises a medical grade plastic. In addition, it is preferred that this internal layer 5 comprises a thermo-sealable material to act as a welding material between the two metal foil layers 4 of the container 1.

The first and second layers 4, 5 are joined together or laminated together in order to act as a single structure which contains on one surface the biocompatibility of the internal layer 5 and the physical properties (i.e. thermo conductivity and semi-rigidity) of the metal foil layer 4. Preferably, the layers 4, 5 are joined together using adhesive means. More preferably, the adhesive means comprises a polymeric adhesive such as a polyester/polyurethane adhesive.

Optionally, the container 1 comprises a third external layer 6, preferably a layer comprising a plastic material. In a preferred embodiment, first layer 4 comprising a metal foil is located between the second layer 5 comprising a biocompatible plastic material and the external layer 6, thereby forming a three layer structure. The addition of this third external layer 6 presents a number of advantages, such as:

1. In the two-layer structure, the first layer 4 comprising a metal foil is exposed. There is therefore a risk of contamination of the heat exchanger by small metal particles being shaved or dislodged during the manufacturing process and falling inside the fluid channel. By adding the third external layer 6, the first layer 4 is sandwiched between two layers of plastic materials and such contamination can be prevented.

2. As strong thermal weld is obtained when the sheet comprises a third external layer 6, so that it can withstand fluid being passed through the channel with the risk of being breached.

Preferably, the external layer 6 comprises a film comprising a material, preferably a polymer material such as polyamide or an oriented polyamide film. Oriented polyamide is most preferred because it offers improvements such as allowing easy printing on its surface. In addition, this external layer 6 may be added to avoid the liberation of potentially toxic metal particles during the manufacturing process.

Preferably, the thickness of the third external layer 6 is preferably less than 35 microns. This layer must be thick enough to provide some integrality and to print onto, but at the same time as thin as possible to ensure good conductivity as it is a natural insulator. More preferably the thickness ranges from 15 microns to 35 microns. The most preferred thickness for the third layer 6 is approximately 25 microns±10%.

This third as well any potential additional layer incorporated to the system should join the first and second layers 4, 5 and act as a single structure as described previously. This external layer 6 is designed to be in contact with the heating plate of the electronic warming or the cooling plates of a cooling unit. It preferably has high biocompatibility and enables relatively easy and clean manipulation during the manufacturing process. It transfers effectively and homogeneously the heat and energy delivered to the system during the welding process of the manufacturing of the heat exchanger.

Preferably, the thickness of the triple layer structure ranges from 90 microns to 170 microns. The most preferred thickness for the triple layer structure including the adhesive is approximately 138 microns±10%.

Coming back to FIG. 1, the first and second layer 4, 5 and optionally third layer 6 or other optional layers, are joined together to form a sheet 7. The container is preferably made of two sheets 7 which are joined together to form a fluid channel 8 to enable the passage of a fluid from the inlet port 2 to the outlet port 3. Preferably, the fluid channel 8 defines a serpentine path.

The fluid channel is obtained preferably by application of vacuum, or mechanical press using pressure to specific areas of the multilayer sheets so as to define its shape, such as the preferred serpentine shape. Because the unique nature of the material it is able to hold the shape when vacuumed or stamped the fluid path is better defined and holds its shape during use. Thus, the fluid can flow through the channel substantially unimpeded, and the homogeneous contact surface between the heat exchanger and the heating/cooling plate is warranted.

Figure 4:
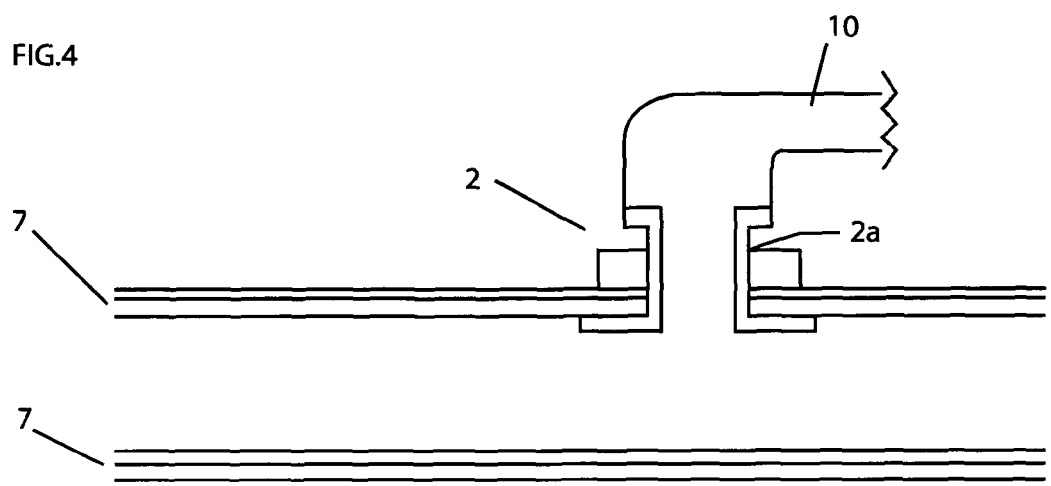
FIG. 4 is a schematic representation of a first fluid connector for a fluid warming or cooling cassette according to the present invention.
Figure 5:
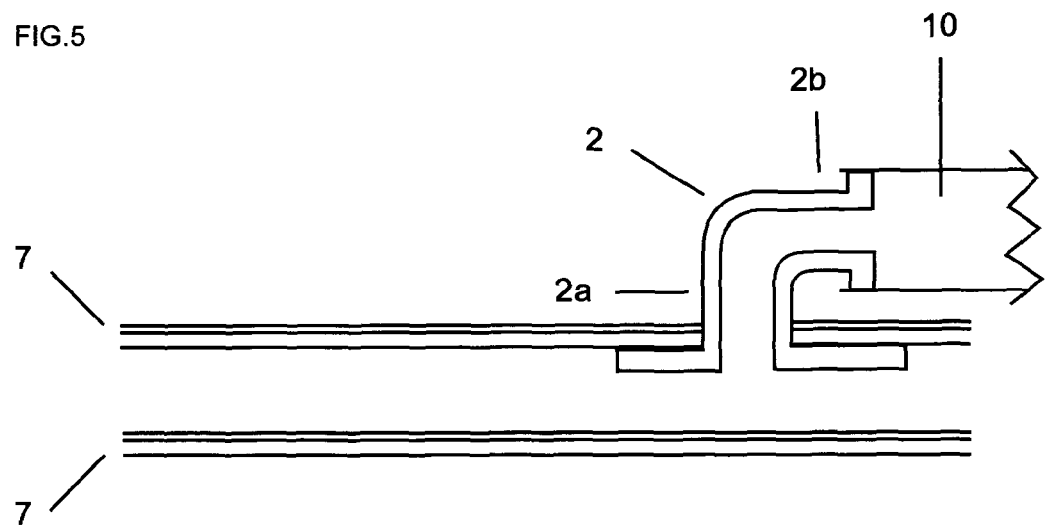
FIG. 5 is a schematic representation of a second fluid connector for a fluid warming or cooling cassette according to the present invention.
Figure 7A:
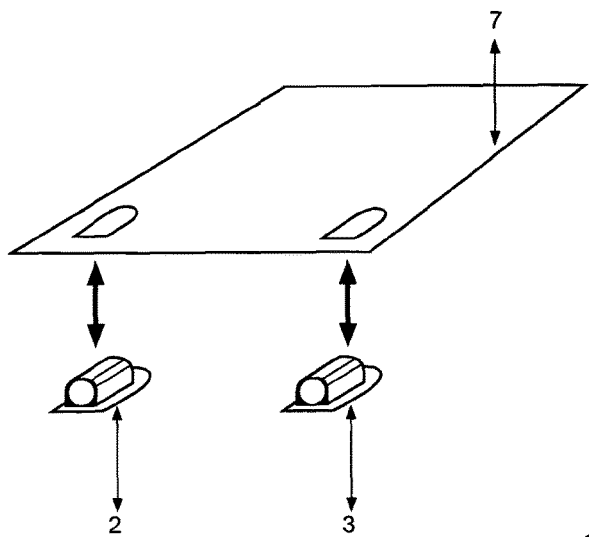
FIGS. 7A and 7B are schematic representations of a third fluid connector for a fluid warming or cooling cassette according to the present invention.
Figure 7B:
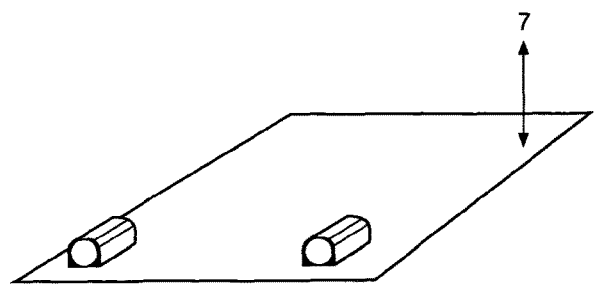

The fluid container 1 may be a generally flat rectangular container. The inlet port 2 and outlet port 3 are preferably located adjacent the edge of the container 1. The port 2, 3 may comprise a first portion 2a extending substantially perpendicularly from the surface of the container 1. Tubing 10 may be connected directly to the end of the first portion 2a (see FIG. 4). Alternatively, port 2, 3 may comprise a second portion 2b extending substantially perpendicularly from the end of the first portion 2a (or substantially parallel to the surface of the container 1) and tubing 10 may be connected to the end of the second portion 2b (see FIG. 5). The port 2,3 or connector shown in FIG. 5 is preferred because the port-tubing formation is more compact and occupies less space than that shown in FIG. 4. The most preferred connectors 2, 3 are shown in FIGS. 7A and 7B, which are constructed and arranged so that the tubing extends along the surface of the container, as opposed to perpendicularly to the surface of the container.

Figure 8A:
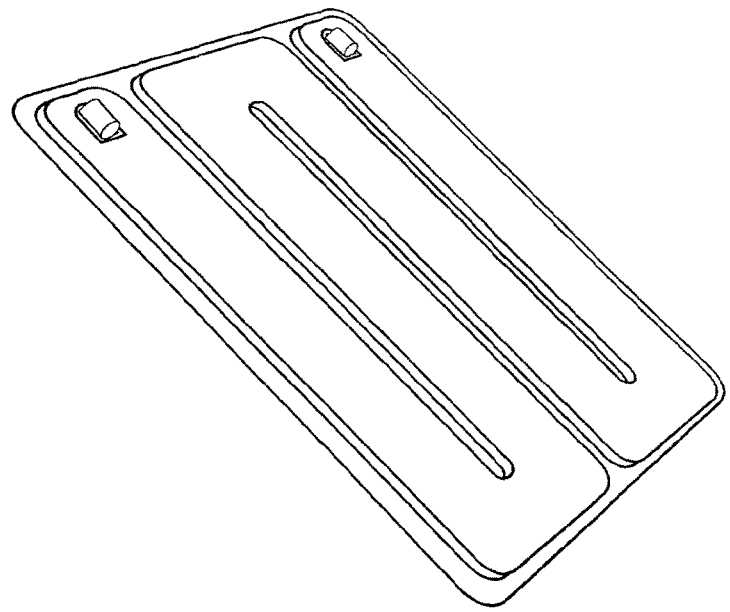
FIGS. 8A to 8C are schematic representations of a third fluid warming or cooling container according to the present invention.
Figure 8B:
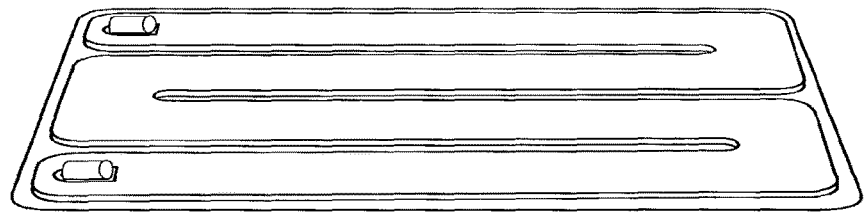
Figure 8C:
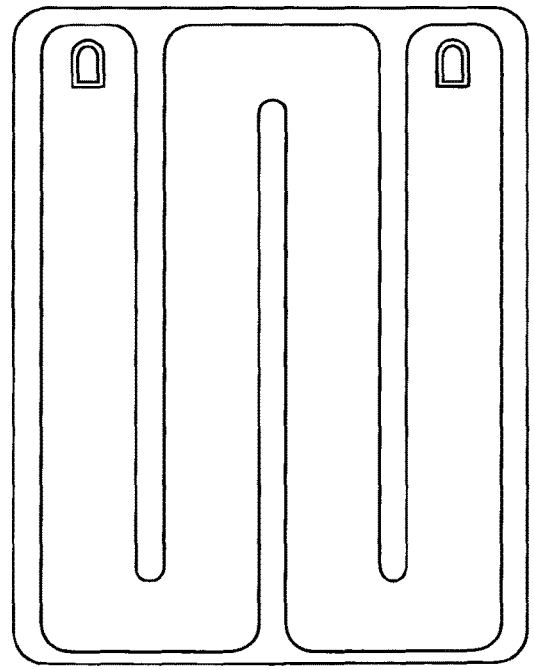
Figure 9:
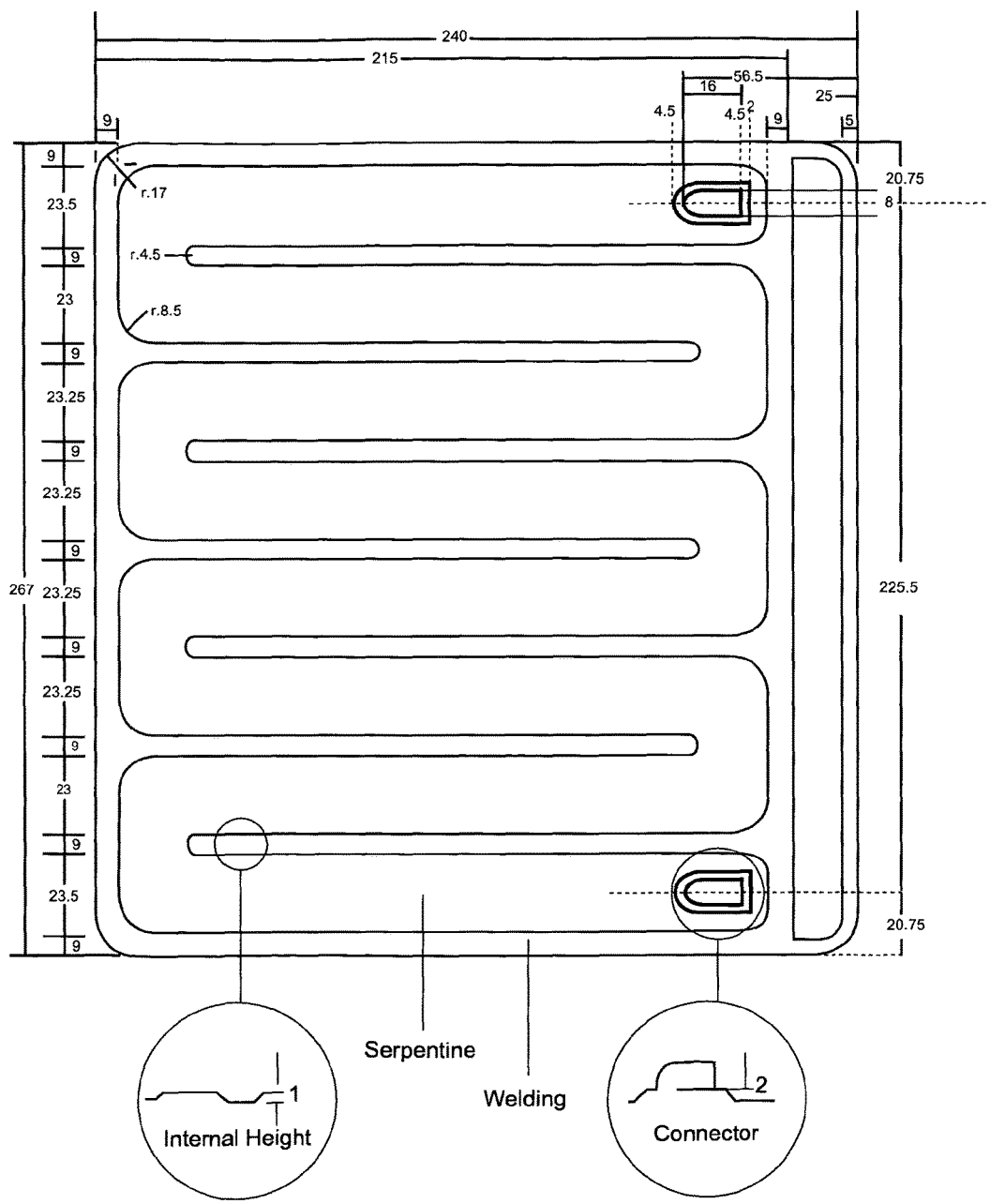
FIG. 9 is a schematic representation of a fourth fluid container according to the present invention.
Figure 10:
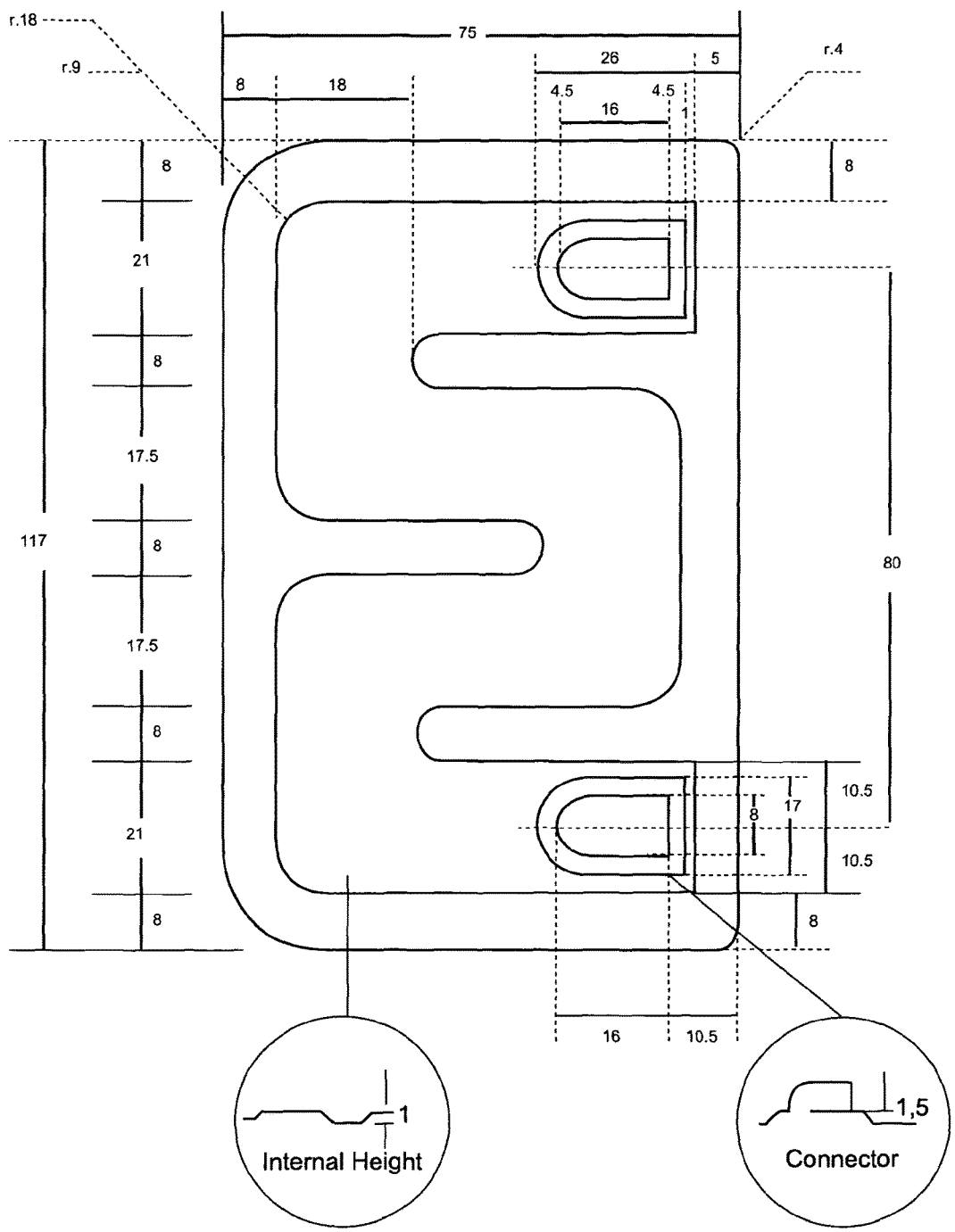
FIG. 10 is a schematic representation of a fifth fluid container according to the present invention.
Figure 11:
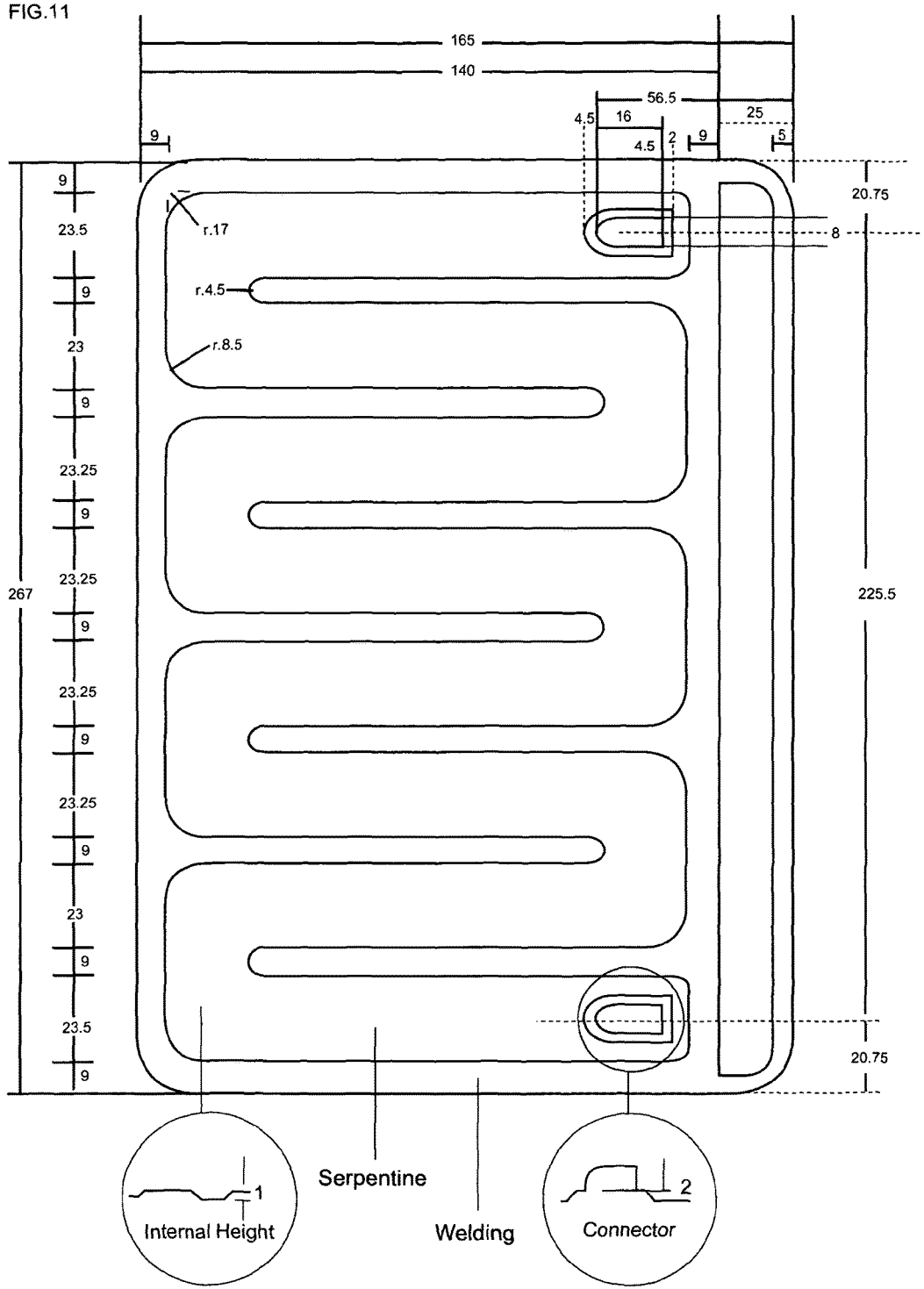
FIG. 11 is a schematic representation of a sixth fluid container according to the present invention.
Figure 12:
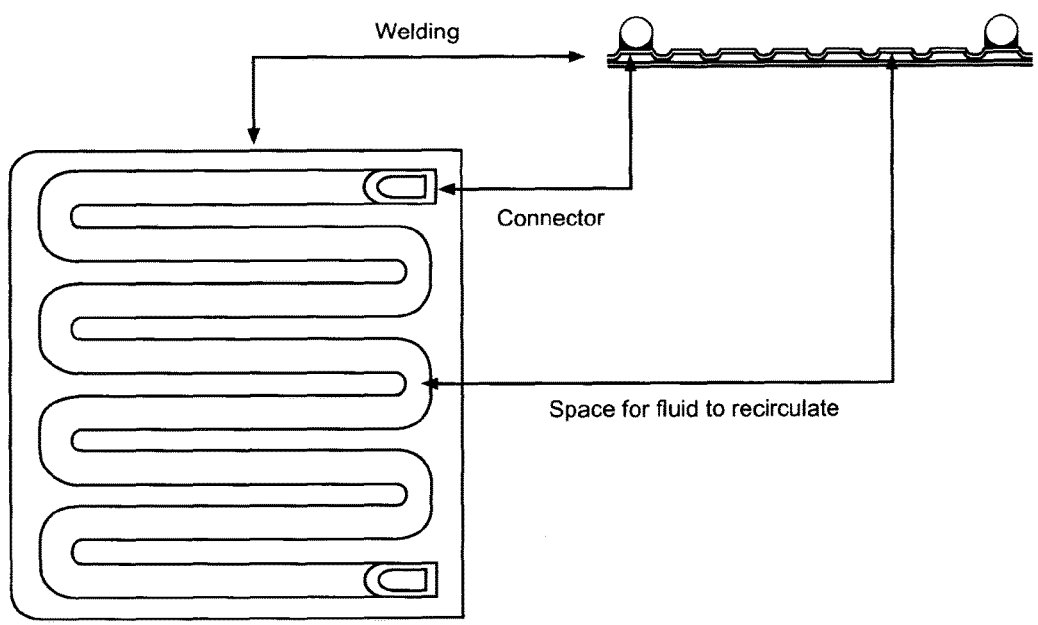
FIG. 12 is a schematic representation of a seventh fluid container according to the present invention.

With reference for example to FIGS. 8A to 8C, the fluid warming or cooling container of the present invention may comprise a fluid channel 8 defining a serpentine path. Because of its physical properties, the multilayer film which includes metal foil can easily be shaped in any required form. Technologies involving for example, vacuum forming, thermal forming or positive pressure apparatus may be used. The serpentine form is preferred as it increases the surface area and therefore improves the conductivity.

Figure 13A:
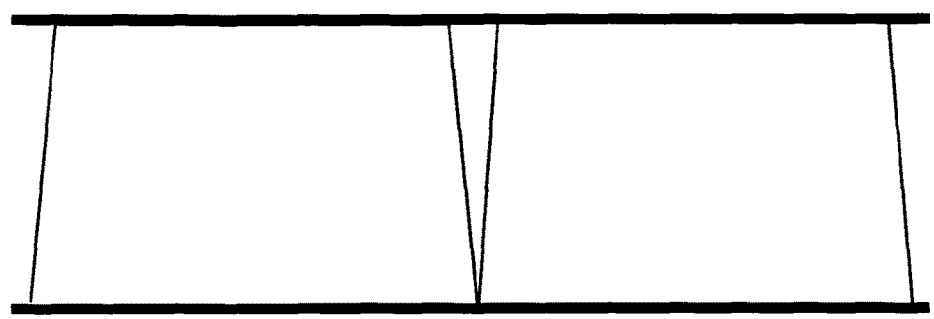
FIG. 13A is a schematic representation of a cross section of a fluid channel of a plastic fluid warming or cooling container.

Another feature increasing the surface area and therefore the conductivity is the substantially flat surface of the fluid warming or cooling container contacting the heating plate of the warming device (or the cooling plate of the cooling device). As can be seen in FIG. 13A, known plastic fluid warming containers have a generally circular, or curved, cross section. Because of the flexibility of the plastic materials used to prepare those containers, the fluid channel will have a tendency to form a circular or curved, shape as it is filled with fluid. Thus the area of the fluid channel actually contacting the heating plate of the warming device is significantly reduced.

Figure 13B:
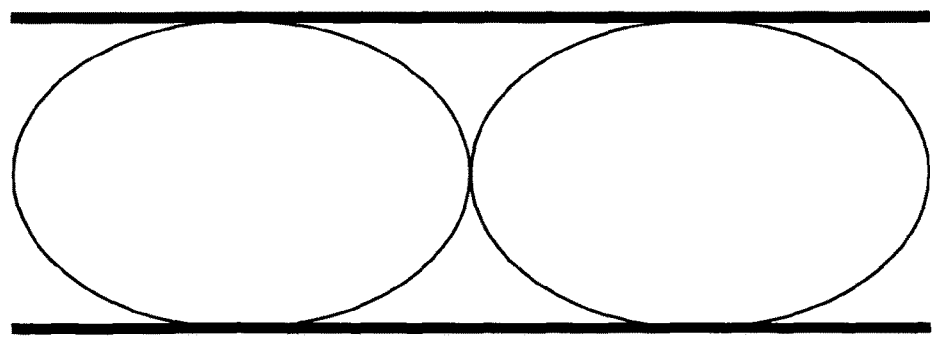
FIG. 13B is a schematic representation of a cross section of a fluid channel of fluid warming or cooling container according to the invention.

By contrast, the fluid warming container of the present invention may comprise fluid channel 8 with at least one substantially flat surface for contacting the heating plate of the warming device or the cooling plate of the cooling device (see FIG. 13B). The container comprises a metal layer which provides the required malleability but also rigidity to produce such a surface. It is possible to achieve a similar shape and rigidity using different material combinations however in order to do so it is likely the container would have to increase in thickness, in doing so would compromised the design and effect heat transfer.

Preferably, the fluid channel 8 has a rounded serpentine shape, i.e. without any angles t facilitate the flow of fluids (see for example the containers of FIGS. 8-12).

In use, the therapeutic fluid is contained in, for example, a fluid bag hooked onto a fluid bag holder. The fluid bag is in fluid communication with the inlet port 2 of the container 1, for example via a plastic tube 10. The outlet port 3 of the container 1 is in fluid communication with the patient for example via a second plastic tube 10. The container 1 is inserted into a fluid warming device, which comprises heating means, preferably two heating plates. The fluid is circulated using pump means or gravity from the fluid bag to the inlet port 2 of the container 1. The fluid flows through the serpentine fluid channel 8 and is heated to a suitable temperature by heat transfer from the heating plates through the sheets 7 of the container 1. The temperature of the fluid may be adjusted using temperature control means, for example, as those described in the Applicant's own British patent application GB 1021898.0. The heated fluid exits the container 1 via outlet port 3 and is delivered to the patient via tubing 10.

Alternatively, the container 1 is inserted into a fluid cooling device, which comprises cooling means, which could be two cooling plates or a bath of cooled or warmed fluid. The fluid flows through the serpentine fluid channel 8 and is cooled to a suitable temperature by heat transfer from therapeutic fluid to the cooling means through the sheets 7 of the container 1. The cooled fluid exits the container 1 via outlet port 3 and is delivered to the patient via tubing 10.

The present invention provides a high performance fluid warming system, with a container with improved heat transfer properties, mostly due to the reduced thickness of the plastic material (which is a poorly conductive material), to the superior heat transfer properties of the metal foil layer, and to the correct rigidity to provide homogeneous and effective contact surface between the heating plates of the fluid warming unit (or the cooling plates of the fluid cooling unit) and the fluid container in the heat exchanger.

The container of the present invention is advantageous in that the multilayer structure is able to slightly expand during use so that it meets the heating plates and ensure an improved transfer of heat and good warming performance. Another advantage arising from this ability to control the expansion is that it is possible to remove the heat exchanger container from in between the two heating plates without having to empty the container of fluid, i.e. to "de-prime" the container. The container expands enough to ensure good contact with the heating plates and not too much so that it cannot be removed from the warming device. The container can therefore be taken out of the warming system after the procedure without having to disconnect the fluid bag in the operating room and then to re-insert the fluid bag into another recovery system in the recovery room. By contrast, when a heat exchanger is made of a material mix that allows for expansion, the container is under pressure when filled with fluid and cannot be removed from the warming device without de-priming.

The production process is simplified and therefore manufacturing costs are reduced for example because easy and homogeneous welding of the multilayer foil is possible. Furthermore, no additional structure (e.g. frames) is required to support the container to facilitate the insertion into the heat warming or cooling unit. In addition, the materials used to manufacture the container of the present invention are relatively inexpensive materials.

EXAMPLE

An example of a multilayer structure for a container according to the invention is provided:

| Material | Thickness, microns | Weight g\m² | Tolerance± |
|---|---|---|---|
| Oriented Polyamide Film | 25 | 28.80 | 10% |
| Adhesive, polyester\polyurethane | | 4.00 | 0.50 |
| Aluminium Soft Foil purity 98% min. | 45 | 121.50 | 8% |
| Adhesive, polyester\polyurethane | | 4.00 | 0.50 |
| PVC Rigid Film | 60 | 79.20 | 10% |
| Overall | 138 | 237.50 | 10% |

Figure 6:
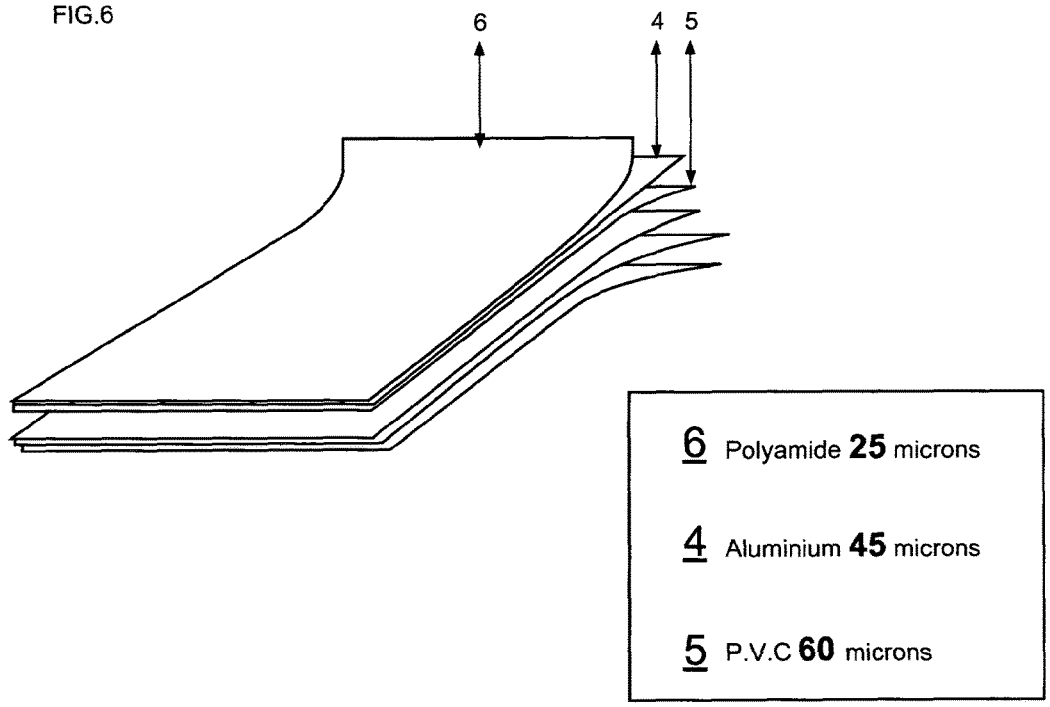
FIG. 6 is a schematic representation of the different layers of a second fluid container according to the present invention.

A three-layer sheet structure with preferred thicknesses (microns) is shown in FIG. 6.

The structure once it has completed at least one sterilization process according to medically required standards has a shelf life of up to five years when properly stored. In terms of storage, the presence of the biocompatible material in the structure of the present invention ensures that there is no leakage from the metal foil layer when therapeutic fluid is passed through the container. The presence of the external layer provides additional protection of the content of the container.

The invention claimed is:

1. A multilayer fluid heat exchanger container comprising more than one thereto-conductive sheet portions, each sheet portion comprising at least a first layer comprising a metal foil between a second internal layer comprising a biocompatible plastic material and a third external layer comprising a biocompatible plastic material, wherein the first layer has a thickness of less than 60 microns and more than 30 microns and wherein the second layer has a thickness of less than 75 microns and more than 45 microns.

2. The container according to claim 1, wherein the first layer comprises aluminium foil.

3. The container according to claim 1, wherein the first layer has a thickness of 45 microns±8%.

4. The container according to claim 1, wherein the second layer comprises a PVC film.

5. The container according to claim 1, wherein the second layer has a thickness of 60 microns±10%.

6. The container according to 1, wherein the biocompatible plastic material comprises an oriented polyamide film.

7. The container according to claim 6, wherein the third layer has a thickness of less than 35 microns and more than 15 microns.

8. The container according to claim 7, wherein the third layer has a thickness of 25 microns±10%.

9. The container according to claim 1, wherein the container comprises two sheets as at least a part of the more than one sheet portions and further comprises a fluid channel formed between said two sheets.

10. The container according to claim 9, preformed according to a shape wherein the fluid channel comprises at least one flat surface for contacting a heating plate of a warming device.

11. A multilayer sheet for a fluid container as defined in claim 1.

12. A system for heating a fluid comprising a fluid container as claimed in claim 1 and a fluid warming device for receiving the fluid container.

13. The container according to claim 4, wherein the PVC film is a medical grade PVC.

14. A system for cooling a fluid comprising a fluid container as claimed in claim 1 and a fluid cooling device for receiving the fluid container.

15. A method for heating a fluid comprising the step of circulating a fluid through a container as claimed in claim 1.

16. A method for cooling a fluid comprising the step of circulating a fluid through a container as claimed in claim 1.

17. A process for the manufacture of a container according to claim 1, comprising the step of providing plural sheet portions, with each sheet portion comprising at least a first layer comprising a metal foil and at least a second internal layer comprising a biocompatible plastic material, and a third external layer comprising a biocompatible plastic material, wherein the first layer has a thickness of less than 60 microns and more than 30 microns and wherein the second layer has a thickness of less than 75 microns and more than 45 microns.

18. The process according to claim 17, wherein a fluid channel is formed by application of vacuum or mechanical press using pressure.

* * * * *